(12) United States Patent
Milner

(10) Patent No.: US 7,863,436 B2
(45) Date of Patent: Jan. 4, 2011

(54) INDUCTION OF APOPTOSIS BY INHIBITION OF SIRTUIN SIRT1 EXPRESSION

(75) Inventor: Anne Josephine Milner, Yorkshire (GB)

(73) Assignee: The University of York, Yorkshire (GB)

( * ) Notice: Subject to any disclaimer, the term of this patent is extended or adjusted under 35 U.S.C. 154(b) by 861 days.

(21) Appl. No.: 10/589,253

(22) PCT Filed: Feb. 11, 2005

(86) PCT No.: PCT/GB2005/000459

§ 371 (c)(1), (2), (4) Date: Apr. 25, 2007

(87) PCT Pub. No.: WO2005/078091

PCT Pub. Date: Aug. 25, 2005

(65) Prior Publication Data

US 2007/0197459 A1    Aug. 23, 2007

(30) Foreign Application Priority Data

Feb. 11, 2004  (GB) ................................ 0403041.7

(51) Int. Cl.
C07H 21/04 (2006.01)
C07H 21/02 (2006.01)
A61K 48/00 (2006.01)

(52) U.S. Cl. ........................ 536/24.5; 536/23.1; 514/44

(58) Field of Classification Search ........................ None
See application file for complete search history.

(56) References Cited

U.S. PATENT DOCUMENTS

2003/0082668 A1* 5/2003 Tamai et al. .................. 435/24

2003/0124101 A1 7/2003 Gu et al.
2005/0136429 A1* 6/2005 Guarente et al. ............... 435/6

FOREIGN PATENT DOCUMENTS

WO        01/51051 A     7/2001

OTHER PUBLICATIONS

Scherer et al., Approaches for the sequence-specific knockdown of mRNA, 2003, Nat. Biotechnol., 21(12), pp. 1457-1465.*
Mahato et al., Modulation of gene expression by antisense and antigene oligodeoxynucleotides and small interfering RNA, Jan. 2005, Expert Opinion on Drug Delivery, vol. 2, No. 1, pp. 3-28.*
Zhang et al., Targeted Gene Silencing by Small Interfering RNA-Based Knock-Down Technology, 2004, Current Pharmaceutical Biotechnology, vol. 5, p. 1-7.*
Grozinger et al., "Deacetylase enzymes: Biological functions and the use of small-molecule inhibitors", Chemistry and Biology, vol. 9, No. 1, Jan. 2002, pp. 3-16, XP00233015.
International Search Report of PCT/GB2005/000459, mailed Jun. 14, 2005.
Grozinger et al., "Deacetylase enzymes: Biological functions and the use of small-molecule inhibitors", Chemistry and Biology, vol. 9, No. 1, Jan. 2002, pp. 3-16, XP00233015.

* cited by examiner

Primary Examiner—Amy Bowman
(74) Attorney, Agent, or Firm—Nixon & Vanderhye P.C.

(57) ABSTRACT

The invention relates to the induction of apoptosis by inhibition of the sirtuin SIRT1 expression, in particular the induction of apoptosis in tumour cells. Materials and methods for inhibiting SIRT1 expression are provided, including RNA interference methods. In particular, the invention provides a method of treating a proliferative disease comprising administering to an individual in need thereof an effective amount of a SIRT1 inhibitor.

3 Claims, No Drawings

SEQUENCE LISTING

<160> NUMBER OF SEQ ID NOS: 17

<210> SEQ ID NO 1
<211> LENGTH: 2241
<212> TYPE: DNA
<213> ORGANISM: Homo sapiens

<400> SEQUENCE: 1

```
atggcggacg aggcggccct cgcccttcag cccggcggct cccctcggc ggcggggcc        60
gacagggagg ccgcgtcgtc ccccgccggg gagccgctcc gcaagaggcc gcggagagat      120
ggtcccggcc tcgagcggag cccgggcgag cccggtgggg cggccccaga gcgtgaggtg      180
ccggcggcgg ccaggggctg cccgggtgcg gcggcggcgg cgctgtggcg ggaggcggag      240
gcagaggcgg cggcggcagg cggggagcaa gaggcccagg cgactgcggc ggctggggaa      300
ggagacaatg gccgggcct gcagggccca tctcgggagc caccgctggc cgacaacttg      360
tacgacgaag acgacgacga cgagggcgag gaggaggaag aggcggcggc ggcggcgatt      420
gggtaccgag ataaccttct gttcggtgat gaaattatca ctaatggttt tcattcctgt      480
gaaagtgatg aggaggatag agcctcacat gcaagctcta gtgactggac tccaaggcca      540
cggataggtc catatacttt tgttcagcaa catcttatga ttggcacaga tcctcgaaca      600
attcttaaag atttattgcc ggaaacaata cctccacctg agttggatga tatgacactg      660
tggcagattg ttattaatat ccttttcagaa ccaccaaaaa ggaaaaaaag aaaagatatt      720
aatacaattg aagatgctgt gaaattactg caagagtgca aaaaaattat agttctaact      780
ggagctgggg tgtctgtttc atgtggaata cctgacttca ggtcaaggga tggtatttat      840
gctcgccttg ctgtagactt cccagatctt ccagatcctc aagcgatgtt tgatattgaa      900
tatttcagaa aagatccaag accattcttc aagtttgcaa ggaaatata tcctggacaa      960
ttccagccat ctctctgtca caaattcata gccttgtcag ataaggaagg aaaactactt     1020
```

```
cgcaactata cccagaacat agacacgctg aacaggttg cgggaatcca aggataatt    1080 cagtgtcatg gttcctttgc aacagcatct tgcctgattt gtaaatacaa agttgactgt    1140
gaagctgtac gaggagatat ttttaatcag gtagttcctc gatgtcctag gtgcccagct    1200
gatgaaccgc ttgctatcat gaaaccagag attgtgtttt ttggtgaaaa tttaccagaa    1260
cagtttcata gagccatgaa gtatgacaaa gatgaagttg acctcctcat tgttattggg    1320
tcttccctca agtaagacc agtagcacta attccaagtt ccatacccca tgaagtgcct    1380
cagatattaa ttaatagaga acctttgcct catctgcatt ttgatgtaga gcttcttgga    1440
gactgtgatg tcataattaa tgaattgtgt cataggttag gtggtgaata tgccaaactt    1500
tgctgtaacc ctgtaaagct ttcagaaatt actgaaaaac ctccacgaac acaaaaagaa    1560
ttggcttatt tgtcagagtt gccacccaca cctcttcatg tttcagaaga ctcaagttca    1620
ccagaaagaa cttcaccacc agattcttca gtgattgtca cacttttaga ccaagcagct    1680
aagagtaatg atgatttaga tgtgtctgaa tcaaaaggtt gtatggaaga aaaaccacag    1740
gaagtacaaa cttctaggaa tgttgaaagt attgctgaac agatggaaaa tccggatttg    1800
aagaatgttg gttctagtac tggggagaaa aatgaaagaa cttcagtggc tggaacagtg    1860
agaaaatgct ggcctaatag agtggcaaag gagcagatta gtaggcggct tgatggtaat    1920
cagtatctgt ttttgccacc aaatcgttac attttccatg cgctgaggt atattcagac    1980 tctgaagatg acgtcttatc ctctagttct tgtggcagta acagtgatag tgggacatgc    2040
cagagtccaa gtttagaaga acccatggag gatgaaagtg aaattgaaga attctacaat    2100
ggcttagaag atgagcctga tgttccagag agagctggag gagctggatt tgggactgat    2160
ggagatgatc aagaggcaat taatgaagct atatctgtga acaggaagt aacagacatg    2220 aactatccat caaacaaatc a    2241
```

<210> SEQ ID NO 2
<211> LENGTH: 747
<212> TYPE: PRT
<213> ORGANISM: Homo sapiens

<400> SEQUENCE: 2

```
Met Ala Asp Glu Ala Ala Leu Ala Leu Gln Pro Gly Gly Ser Pro Ser
1               5                   10                  15

Ala Ala Gly Ala Asp Arg Glu Ala Ala Ser Ser Pro Ala Gly Glu Pro
                20                  25                  30

Leu Arg Lys Arg Pro Arg Arg Asp Gly Pro Gly Leu Glu Arg Ser Pro
            35                  40                  45

Gly Glu Pro Gly Gly Ala Ala Pro Glu Arg Glu Val Pro Ala Ala Ala
        50                  55                  60

Arg Gly Cys Pro Gly Ala Ala Ala Ala Leu Trp Arg Glu Ala Glu
65                  70                  75                  80

Ala Glu Ala Ala Ala Gly Gly Glu Gln Glu Ala Gln Ala Thr Ala
                85                  90                  95

Ala Ala Gly Glu Gly Asp Asn Gly Pro Gly Leu Gln Gly Pro Ser Arg
            100                 105                 110

Glu Pro Pro Leu Ala Asp Asn Leu Tyr Asp Glu Asp Asp Asp Asp Glu
        115                 120                 125

Gly Glu Glu Glu Glu Glu Ala Ala Ala Ala Ile Gly Tyr Arg Asp
    130                 135                 140

Asn Leu Leu Phe Gly Asp Glu Ile Ile Thr Asn Gly Phe His Ser Cys
145                 150                 155                 160
```

```
Glu Ser Asp Glu Glu Asp Arg Ala Ser His Ala Ser Ser Ser Asp Trp
            165                 170                 175

Thr Pro Arg Pro Arg Ile Gly Pro Tyr Thr Phe Val Gln Gln His Leu
        180                 185                 190

Met Ile Gly Thr Asp Pro Arg Thr Ile Leu Lys Asp Leu Leu Pro Glu
            195                 200             205

Thr Ile Pro Pro Glu Leu Asp Asp Met Thr Leu Trp Gln Ile Val
    210                 215             220

Ile Asn Ile Leu Ser Glu Pro Pro Lys Arg Lys Arg Lys Asp Ile
225             230              235              240

Asn Thr Ile Glu Asp Ala Val Lys Leu Leu Gln Glu Cys Lys Lys Ile
            245                 250                 255

Ile Val Leu Thr Gly Ala Gly Val Ser Val Ser Cys Gly Ile Pro Asp
            260                 265                 270

Phe Arg Ser Arg Asp Gly Ile Tyr Ala Arg Leu Ala Val Asp Phe Pro
        275                 280                 285

Asp Leu Pro Asp Pro Gln Ala Met Phe Asp Ile Glu Tyr Phe Arg Lys
    290                 295                 300

Asp Pro Arg Pro Phe Phe Lys Phe Ala Lys Glu Ile Tyr Pro Gly Gln
305                 310                 315                 320

Phe Gln Pro Ser Leu Cys His Lys Phe Ile Ala Leu Ser Asp Lys Glu
            325                 330                 335

Gly Lys Leu Leu Arg Asn Tyr Thr Gln Asn Ile Asp Thr Leu Glu Gln
            340                 345                 350

Val Ala Gly Ile Gln Arg Ile Ile Gln Cys His Gly Ser Phe Ala Thr
            355                 360                 365

Ala Ser Cys Leu Ile Cys Lys Tyr Lys Val Asp Cys Glu Ala Val Arg
        370                 375                 380

Gly Asp Ile Phe Asn Gln Val Val Pro Arg Cys Pro Arg Cys Pro Ala
385                 390                 395                 400

Asp Glu Pro Leu Ala Ile Met Lys Pro Glu Ile Val Phe Phe Gly Glu
            405                 410                 415

Asn Leu Pro Glu Gln Phe His Arg Ala Met Lys Tyr Asp Lys Asp Glu
            420                 425                 430

Val Asp Leu Leu Ile Val Ile Gly Ser Ser Leu Lys Val Arg Pro Val
        435                 440                 445

Ala Leu Ile Pro Ser Ser Ile Pro His Glu Val Pro Gln Ile Leu Ile
    450                 455                 460

Asn Arg Glu Pro Leu Pro His Leu His Phe Asp Val Glu Leu Leu Gly
465                 470                 475                 480

Asp Cys Asp Val Ile Ile Asn Glu Leu Cys His Arg Leu Gly Gly Glu
            485                 490                 495

Tyr Ala Lys Leu Cys Cys Asn Pro Val Lys Leu Ser Glu Ile Thr Glu
            500                 505                 510

Lys Pro Pro Arg Thr Gln Lys Glu Leu Ala Tyr Leu Ser Glu Leu Pro
        515                 520                 525

Pro Thr Pro Leu His Val Ser Glu Asp Ser Ser Ser Pro Glu Arg Thr
    530                 535                 540

Ser Pro Pro Asp Ser Ser Val Ile Val Thr Leu Leu Asp Gln Ala Ala
545                 550                 555                 560

Lys Ser Asn Asp Asp Leu Asp Val Ser Glu Ser Lys Gly Cys Met Glu
            565                 570                 575
```

-continued

```
Glu Lys Pro Gln Glu Val Gln Thr Ser Arg Asn Val Glu Ser Ile Ala
            580                 585                 590
Glu Gln Met Glu Asn Pro Asp Leu Lys Asn Val Gly Ser Ser Thr Gly
        595                 600                 605
Glu Lys Asn Glu Arg Thr Ser Val Ala Gly Thr Val Arg Lys Cys Trp
    610                 615                 620
Pro Asn Arg Val Ala Lys Glu Gln Ile Ser Arg Arg Leu Asp Gly Asn
625                 630                 635                 640
Gln Tyr Leu Phe Leu Pro Pro Asn Arg Tyr Ile Phe His Gly Ala Glu
            645                 650                 655
Val Tyr Ser Asp Ser Glu Asp Val Leu Ser Ser Ser Cys Gly
        660                 665                 670
Ser Asn Ser Asp Ser Gly Thr Cys Gln Ser Pro Ser Leu Glu Glu Pro
    675                 680                 685
Met Glu Asp Glu Ser Glu Ile Glu Glu Phe Tyr Asn Gly Leu Glu Asp
690                 695                 700
Glu Pro Asp Val Pro Glu Arg Ala Gly Gly Ala Gly Phe Gly Thr Asp
705                 710                 715                 720
Gly Asp Asp Gln Glu Ala Ile Asn Glu Ala Ile Ser Val Lys Gln Glu
            725                 730                 735
Val Thr Asp Met Asn Tyr Pro Ser Asn Lys Ser
            740                 745

<210> SEQ ID NO 3
<211> LENGTH: 21
<212> TYPE: DNA
<213> ORGANISM: Artificial sequence
<220> FEATURE:
<223> OTHER INFORMATION: SIRT1 sense primer

<400> SEQUENCE: 3
tcagtgtcat ggttcctttg c                                          21

<210> SEQ ID NO 4
<211> LENGTH: 21
<212> TYPE: DNA
<213> ORGANISM: Artificial sequence
<220> FEATURE:
<223> OTHER INFORMATION: SIRT1 antisense primer

<400> SEQUENCE: 4
aatctgctcc tttgccactc t                                          21

<210> SEQ ID NO 5
<211> LENGTH: 21
<212> TYPE: DNA
<213> ORGANISM: Artificial sequence
<220> FEATURE:
<223> OTHER INFORMATION: Lamin A sense primer

<400> SEQUENCE: 5
aagcagcgtg agtttgagag c                                          21

<210> SEQ ID NO 6
<211> LENGTH: 21
<212> TYPE: DNA
<213> ORGANISM: Artificial sequence
<220> FEATURE:
<223> OTHER INFORMATION: Lamin A antisense primer

<400> SEQUENCE: 6
```
agggtgaact ttggtgggaa c    21

<210> SEQ ID NO 7
<211> LENGTH: 24
<212> TYPE: DNA
<213> ORGANISM: Artificial sequence
<220> FEATURE:
<223> OTHER INFORMATION: GAPDH sense primer

<400> SEQUENCE: 7
cggagtcaac ggatttggtc gtat    24

<210> SEQ ID NO 8
<211> LENGTH: 24
<212> TYPE: DNA
<213> ORGANISM: Artificial sequence
<220> FEATURE:
<223> OTHER INFORMATION: GAPDH antisense primer

<400> SEQUENCE: 8
agccttctcc atggtggtga agac    24

<210> SEQ ID NO 9
<211> LENGTH: 21
<212> TYPE: DNA
<213> ORGANISM: Artificial sequence
<220> FEATURE:
<223> OTHER INFORMATION: Vimentin sense primer

<400> SEQUENCE: 9
gccaactaca tcgacaaggt g    21

<210> SEQ ID NO 10
<211> LENGTH: 21
<212> TYPE: DNA
<213> ORGANISM: Artificial sequence
<220> FEATURE:
<223> OTHER INFORMATION: Vimentin antisense primer

<400> SEQUENCE: 10
gagcaggtct tggtattcac g    21

<210> SEQ ID NO 11
<211> LENGTH: 21
<212> TYPE: DNA
<213> ORGANISM: Artificial sequence
<220> FEATURE:
<223> OTHER INFORMATION: SIRT1 siRNA sequence

<400> SEQUENCE: 11
acuuugcugu aacccuguat t    21

<210> SEQ ID NO 12
<211> LENGTH: 21
<212> TYPE: DNA
<213> ORGANISM: Artificial sequence
<220> FEATURE:
<223> OTHER INFORMATION: SIRT1 siRNA sequence

<400> SEQUENCE: 12
uacaggguua cagcaaagut t    21

<210> SEQ ID NO 13
<211> LENGTH: 21
<212> TYPE: DNA
<213> ORGANISM: Artificial sequence

```
<220> FEATURE:
<223> OTHER INFORMATION: Lamin A/C siRNA sequence

<400> SEQUENCE: 13
cuggacuucc agaagaacat t                                              21

<210> SEQ ID NO 14
<211> LENGTH: 21
<212> TYPE: DNA
<213> ORGANISM: Artificial sequence
<220> FEATURE:
<223> OTHER INFORMATION: Lamin A/C siRNA sequence

<400> SEQUENCE: 14
uguucuucug gaaguccagt t                                              21

<210> SEQ ID NO 15
<211> LENGTH: 21
<212> TYPE: DNA
<213> ORGANISM: Artificial sequence
<220> FEATURE:
<223> OTHER INFORMATION: BRC-ABL siRNA sequence

<400> SEQUENCE: 15
agaguucaaa agcccuucat t                                              21

<210> SEQ ID NO 16
<211> LENGTH: 21
<212> TYPE: DNA
<213> ORGANISM: Artificial sequence
<220> FEATURE:
<223> OTHER INFORMATION: BRC-ABL siRNA sequence

<400> SEQUENCE: 16
ugaagggcuu uugaacucut t                                              21

<210> SEQ ID NO 17
<211> LENGTH: 2241
<212> TYPE: DNA
<213> ORGANISM: Homo sapiens

<400> SEQUENCE: 17
tgatttgttt gatggatagt tcatgtctgt tacttcctgt ttcacagata tagcttcatt    60
aattgcctct tgatcatctc catcagtccc aaatccagct cctccagctc tctctggaac   120
atcaggctca tcttctaagc cattgtagaa ttcttcaatt tcactttcat cctccatggg   180
ttcttctaaa cttggactct ggcatgtccc actatcactg ttactgccac aagaactaga   240
ggataagacg tcatcttcag agtctgaata taccctcagcg ccatggaaaa tgtaacgatt   300
tggtggcaaa aacagatact gattaccatc aagccgccta ctaatctgct cctttgccac   360
tctattaggc cagcattttc tcactgttcc agccactgaa gttctttcat ttttctcccc   420
agtactagaa ccaacattct tcaaatccgg attttccatc tgttcagcaa tactttcaac   480
attcctagaa gtttgtactt cctgtggttt ttcttccata caaccttttg attcagacac   540
atctaaatca tcattactct tagctgcttg gtctaaaagt gtgacaatca ctgaagaatc   600
tggtggtgaa gttctttctg gtgaacttga gtcttctgaa acatgaagag gtgtgggtgg   660
caactctgac aaataagcca attctttttg tgttcgtgga ggttttttcag taatttctga   720 aagctttaca gggttacagc aaagtttggc atattcacca cctaacctat gacacaattc   780
attaattatg acatcacagt ctccaagaag ctctacatca aaatgcagat gaggcaaagg   840
```

```
ttctctatta attaatatct gaggcacttc atggggtatg gaacttggaa ttagtgctac      900
tggtcttact ttgagggaag acccaataac aatgaggagg tcaacttcat ctttgtcata      960
cttcatggct ctatgaaact gttctggtaa attttcacca aaaaacacaa tctctggttt     1020
catgatagca agcggttcat cagctgggca cctaggacat cgaggaacta cctgattaaa     1080
aatatctcct cgtacagctt cacagtcaac tttgtattta caaatcaggc aagatgctgt     1140
tgcaaaggaa ccatgacact gaattatcct ttggattccc gcaacctgtt ccagcgtgtc     1200
tatgttctgg gtatagttgc gaagtagttt tccttcctta tctgacaagg ctatgaattt     1260
gtgacagaga gatggctgga attgtccagg atatatttcc tttgcaaact tgaagaatgg     1320
tcttggatct tttctgaaat attcaatatc aaacatcgct tgaggatctg gaagatctgg     1380
gaagtctaca gcaaggcgag cataaatacc atcccttgac ctgaagtcag gtattccaca     1440
tgaaacagac accccagctc cagttagaac tataattttt ttgcactctt gcagtaattt     1500
cacagcatct tcaattgtat taatatcttt tctttttttc cttttggtg gttctgaaag      1560
gatattaata acaatctgcc acagtgtcat atcatccaac tcaggtggag gtattgtttc     1620
cggcaataaa tctttaagaa ttgttcgagg atctgtgcca atcataagat gttgctgaac     1680
aaaagtatat ggacctatcc gtggccttgg agtccagtca ctagagcttg catgtgaggc     1740
tctatcctcc tcatcacttt cacaggaatg aaaaccatta gtgataattt catcaccgaa     1800
cagaaggtta tctcggtacc caatcgccgc cgccgccgcc tcttcctcct cctcgccctc     1860
gtcgtcgtcg tcttcgtcgt acaagttgtc ggccagcggt ggctcccgag atgggccctg     1920
caggcccggc ccattgtctc cttccccagc cgccgcagtc gcctgggcct cttgctcccc     1980
gcctgccgcc gccgcctctg cctccgcctc ccgccacagc gccgccgccg ccgcacccgg     2040
gcagcccctg gccgccgccg gcacctcacg ctctggggcc gccccaccgg gctcgcccgg     2100
gctccgctcg aggccgggac catctctccg cggcctcttg cggagcggct ccccggcggg     2160
ggacgacgcg gcctccctgt cggcccccgc cgccgagggg gagccgccgg gctgaagggc     2220
gagggccgcc tcgtccgcca t                                               2241
```

INDUCTION OF APOPTOSIS BY INHIBITION OF SIRTUIN SIRT1 EXPRESSION

This application is the US national phase of international application PCT/GB05/00459, filed 11 Feb. 2005, which designated the U.S. and claims priority of GB 0403041.7, filed 11 Feb. 2004, the entire contents of each of which are hereby incorporated by reference.

FIELD OF THE INVENTION

This invention relates to the induction of apoptosis by inhibition of SIRT1 expression, in particular the induction of apoptosis in tumour cells. Materials and methods for inhibiting SIRT1 expression are provided, including RNA interference methods.

BACKGROUND TO THE INVENTION

Many different types of stress stimulate cellular signalling pathways that result in stabilisation and activation of the tumour suppressor p53 (reviewed in Pluquet and Hainaut, 2001). Stabilisation of p53 is invariably accompanied by extensive post-translational modifications, including phosphorylation and acetylation (see Appella and Anderson, 2001). Mapping the precise relationships between stress stimuli, specific modifications and the stabilisation and activation of p53 has proven extremely difficult; however general patterns and more specific correlations are now established, particularly with regard to phosphorylation of the amino-terminus and acetylation of the carboxy-terminus.

The transcriptional activity of p53, with particular regard to its pro-apoptotic functions, is tightly regulated. Therefore if acetylation functions to activate p53 transcriptional activity, a logical assumption would be that p53 acetylation is subject to negative control.

Until recently, deacetylation of p53 was only known to be performed by members of the trichostatin A-sensitive histone deacetylase (HDAC) class I family (Juan et al., 2000; Luo et al., 2000). Indeed, mounting evidence suggests that p53 utilises these HDACs to repress specific promoters (Murphy et al., 1999). More recently, the human sirtuin SIRT1 (Frye, 1999) has been identified as a bona fide p53 deacetylase (Luo et al., 2001; Vaziri et al., 2001).

The sirtuins are a ubiquitous gene family found throughout eukarya and prokarya, defined by conserved ~250 amino acid core domain. Many of the sirtuins are NAD-dependent deacetylases ['NDAC'].

The function of *Saccharomyces cerevisiae* sirtuin SIR2 has been extensively studied. It has many activities including silencing of mating-type loci, telomeric position effect silencing and silencing at the rDNA locus, suppression of illegitimate recombination and increasing cellular control of longevity. It is also implicated in response to dsDNA breaks.

Humans have seven sirtuins, although not all appear to have NDAC activity.

Human SIRT2 is a cytoplasmic, microtubule-associated protein. Is shows increases in abundance and phosphorylation at G2/M. It is a tubulin deacetylase. and is strongly down-regulated in many gliomas and glioma cell lines. Transgene replacement causes microtubule disruption and strongly reduces the number of stable clones expressing SIRT2 compared to a control in colony formation assays (Hiratsuka, M et al (2003) Biochem Biophys Res Commun. 309(3) 558-566).

Human SIRT3 is synthesized as an inactive proenzyme and activated by proteolysis on insertion into the mitochondrial matrix. Its function is unknown Human SIRT1 is the closest human homologue to yeast SIR2. It is a nuclear protein found throughout the nucleus. Immunostaining of cells with anti-SIRT1 antibodies shows diffuse nuclear staining.

SIRT1 interacts with p53 via the p53 core and carboxy-terminus. It appears to act as a p53 deacetylase, as overexpression of SIRT1 results in reduced acetylation of p53. This in turn leads to reduced expression of endogenous p21, reduced transcription from a p21 reporter construct, and reduced apoptosis in response to $H_2O_2$ and γ-rays.

Overexpression of a catalytically inactive mutant SIRT1 enhances acetylation of p53, and sensitises cells to apoptosis induced by $H_2O_2$ and γ-rays.

The current consensus is that SIRT1 negatively regulates p53 function via deacetylation of p53, so that inhibition of SIRT1 function sensitises cells to p53-dependent apoptosis in response to cellular stress (Luo et al., 2001; Vaziri et al., 2001; Langley et al, 2002)

However, modulation of SIRT1 activity has until now been achieved by treatment of cells with the SIRT1 inhibitor nicotinamide, or by overexpression in trans of wild type and catalytically inactive forms of SIRT1. The use of nicotinamide is problematic, partly due to potential inhibition of the SIRT1-related NDACs and SIRT2 and SIRT3, and partly due to potential pleiotropic effects as nicotinamide is a natural cellular intermediary metabolite. Recent studies have also shown that transgene dosage may be critical in the analysis of p53 function (Blattner et al., 1999; Dumaz et al., 2001), and may underlie the sometimes-conflicting results that have been reported for p53 using this technique.

SUMMARY OF THE INVENTION

In order to elucidate the role of SIRT1 in regulating p53 deacetylation, p53 function and apoptosis, we sought a specific and efficient method of inhibiting the expression or activity of SIRT1.

We addressed the problems of the prior art methods by using a more specific technique, RNA interference, to inhibit SIRT1 expression. RNA interference (RNAi) was used to analyse the function of p53 carboxy-terminal acetylation in p53-dependent apoptosis. The aim was to stabilise acetylation of p53 by silencing of SIRT1. RNAi is a sequence-specific post-translational gene silencing mechanism, which can be initiated in cultured mammalian cells by transfection of a 19-21 nucleotide RNA duplex (short interfering RNA; 'siRNA') homologous in sequence to the target mRNA (Elbashir et al., 2001). Importantly, it has been demonstrated that RNAi does not in itself engage the apoptotic machinery nor alter apoptotic processes, (Jiang and Milner, 2002; Jiang and Milner 2003).

Using RNAi to inhibit SIRT1 expression, we surprisingly found that inhibition of SIRT1 induces massive apoptosis in tumour cells even without additional apoptotic stimuli. This effect is independent of p53 and thus appears to represent a completely new and unexpected activity of SIRT1. It also appears to be independent of the known pro-apoptotic proteins Bax and PUMA.

Even more surprisingly, the induction of apoptosis seen on inhibition of SIRT1 expression by RNAi appears to be specific to tumour cells, as it does not occur in normal human fibroblasts. This opens the way for new approaches to cancer treatment via the specific induction of apoptosis in tumour cells.

Prior to the invention, inhibition of SIRT1 expression would not have been expected to induce apoptosis in tumour cells in preference to normal cells. In fact, the opposite assumption would have been made, as it was thought that SIRT1 acted only on the p53-dependent pathway of apoptosis, and many tumour cells lack functional p53. Further, it would not have been expected that inhibition of SIRT1 expression alone would induce apoptosis in the absence of other stimuli to trigger p53-dependent apoptotic pathways. The observations of the prior art indicated that inhibition of SIRT1 expression would exacerbate the apoptotic phenotype of cells dying in response to agents that activate p53-dependent apoptotic pathways (Luo et al., 2001; Vaziri et al., 2001), but not that loss of SIRT1 expression itself could induce apoptosis in a p53-independent manner The invention accordingly provides for a method of inducing apoptosis in a cell comprising administering a SIRT inhibitor to the cell. Preferably, the cell is a tumour cell. In some embodiments, the cell lacks functional p53, Bax and/or PUMA protein.

The SIRT1 inhibitor may be an agent for inducing RNA interference in a cell, such as a siRNA, a dsRNA, or a nucleic acid encoding such RNA. In a preferred embodiment, said agent is a siRNA.

In another aspect, the invention provides a method of treating a proliferative disease comprising administering to an individual in need thereof an effective amount of a SIRT1 inhibitor. The disease may be cancer, for example a colorectal carcinoma.

Thus, the invention also provides a SIRT1 inhibitor for use in a method of medical treatment or therapy. The therapy may be treatment of a proliferative disease, for example cancer. Also provided is the use of a SIRT1 inhibitor in the manufacture of a medicament for the treatment of a proliferative disease.

In another aspect, the invention provides a method of identifying a SIRT inhibitor for use in a method of treatment of the invention, the method comprising administering a candidate compound to cultured tumour cells in vitro; determining whether SIRT expression and/or activity is reduced in said cells; and assaying for apoptosis of said cells. The method may further comprise a step of administering said candidate compound to cultured non-tumour cells in vitro and assaying for apoptosis of said cells.

In another aspect, the invention provides an agent for inhibiting the expression of SIRT1 protein in a cell. The agent may be an agent which induces RNA interference to SIRT1 mRNA in a cell, for example siRNA, a dsRNA, or a nucleic acid encoding such RNA. In a preferred embodiment, the agent is a siRNA.

Compositions for pharmaceutical use comprising agents of the invention in combination with a pharmaceutically acceptable excipient are also provided.

DETAILED DESCRIPTION

Proteins

SIRT1 refers to human sirtuin 1 as described above. SIRT1 is encoded by a nucleic acid with nucleotide sequence shown in SEQ ID NO:1 in Table 3. The GenBank accession number for the full-length SIRT1 cDNA and its amino acids sequence (SEQ ID NO:2) is NM012238.

Functional p53 protein indicates p53 protein which is capable of inducing apoptosis. A cell lacking functional p53 protein may, for example, carry a deletion or termination mutation of p53 so that it does not express full length p53 at all. Alternatively, the cell may express a mutant p53 which is not capable of triggering apoptosis.

PUMA (p53 upregulated modulator of apoptosis) is a mitochondrial protein that appears to be required for p53-mediated apoptosis (Yu et al., 2003). Expression of PUMA is tightly regulated by p53. PUMA triggers apoptosis via Bax by binding to Bcl-2 and Bcl-$X_L$, which otherwise bind and sequester Bax.

Bax is member of the Bcl-2 family of apoptosis regulatory proteins which induces apoptosis, at least in part by triggering release of cytochrome c from mitochondria. Cytochrome c mediates the subsequent activation of the caspases which carry out the apoptotic death programme. Expression of Bax may also be upregulated by p53.

SIRT1 Inhibitor

The term 'SIRT1 inhibitor' is intended to cover any agent that reduces the expression or activity of SIRT1 in a cell. Alternatively, the agent may be an agent that inhibits the transcription or translation of SIRT, such as an antisense DNA, RNA or an agent that induces RNA interference. Inhibition of SIRT expression may be detected by RT-PCR using SIRT1-specific primers, or by Western blotting using an anti-SIRT1 antibody.

RNA Interference

RNA interference (RNAi) is a process whereby the introduction of double stranded RNA (dsRNA) into a cell inhibits gene expression post-transcriptionally, in a sequence dependent fashion. This process is also known as post-transcriptional gene silencing. Current models of RNAi indicate that it is mediated by short (typically 20-25 nucleotides) dsRNAs known as 'small interfering RNAs' (siRNA). It appears that dsRNA is cleaved in the cell to create siRNAs. siRNAs are then incorporated into an RNA-induced silencing complex (RISC), guiding the complex to the homologous endogenous mRNA. The activated RISC then cleaves the mRNA transcript, resulting in the destruction of the mRNA in a cell which is homologous to the siRNAs. The siRNAs are recycled. In this way, a relatively small number of siRNAs can selectively destroy a large excess of cellular mRNA.

To induce RNA interference in a cell, dsRNA may be introduced into the cell as an isolated nucleic acid fragment or via a transgene, plasmid or virus. Alternatively, siRNA may be synthesised and introduced directly into the cell.

siRNA sequences are selected on the basis of their homology to the gene it is desired to silence. Homology between two nucleotide sequences may be determined using a variety of programs including the BLAST program, of Altschul et al. (1990) *J. Mol. Biol.* 215: 403-10, or BestFit, which is part of the Wisconsin Package, Version 8, September 1994, (Genetics Computer Group, 575 Science Drive, Madison, Wis., USA, Wisconsin 53711). Sequence comparisons may be made using FASTA and FASTP (see Pearson & Lipman, 1988. Methods in Enzymology 183: 63-98). Parameters are preferably set, using the default matrix, as follows: Gapopen (penalty for the first residue in a gap): −16 for nucleic acid; Gapext (penalty for additional residues in a gap): −4 for nucleic acids; KTUP word length: 6 for nucleic acids.

Sequence comparison may be made over the full length of the relevant sequence, or may more preferably be over a contiguous sequence of about or 10, 15, 20, 25 or 30 bases.

Preferably the degree of homology between the siRNA and the target gene is at least 75%, at least 80%, at least 85%, at least 90%, at least 95%, at least 97%, or at least 99%.

The degree of homology between the siRNA or dsRNA and the gene to be silenced will preferably be sufficient that the siRNA or dsRNA will hybridise to the nucleic acid of the gene sequence under stringent hybridisation conditions.

Typical hybridisation conditions use 4-6×SSPE; 5-10× Denhardts solution, 5 g polyvinylpyrrolidone and 5 g bovine serum albumin; 100 μg-lmg/ml sonicated salmon sperm DNA; 0.1-1% sodium dodecyl sulphate; optionally 40-60% deionised formamide. Hybridisation temperature will vary depending on the GC content of the nucleic acid target sequence but will typically be between 42° C.-65° C. Sambrook et al (2001) Molecular Cloning: A Laboratory Approach ($3^{rd}$ Edn, Cold Spring Harbor Laboratory Press). A common formula for calculating the stringency conditions required to achieve hybridisation between nucleic acid molecules of a specified homology is:

$$T_m = 81.5°\text{ C.} + 16.6 \text{ Log } [\text{Na}^+] + 0.41[\% \text{ } G+C] - 0.63(\% \text{ formamide}).$$

The siRNA may be between 10 bp and 30 bp in length, preferably between 20 bp and 25 bp. Preferably, the siRNA is 19, 20, 21 or 22 bp in length.

The siRNA sequence may be, for example, any suitable contiguous sequence of 10-30 bp from the sequence shown in Table 3 (SEQ ID No. 1). Alternatively, longer dsRNA fragments comprising contiguous sequences from the sequences of SEQ ID NO. 1 may be used, as they will be cleaved to form siRNAs within the cell. Preferably, the siRNA sequence is that shown in Table 2 (SEQ ID NOs:11 & 12).

In a preferred embodiment, the siRNA has the 19 bp sequence shown in Table 2. In some embodiments, the siRNA has an overhang at one or both ends of one or more deoxythymidine bases. The overhang is not to be interpreted as part of the siRNA sequence. Where present, it serves to increase the stability of the siRNA within cells by reducing its susceptibility to degradation by nucleases.

siRNA molecules may be synthesized using standard solid or solution phase synthesis techniques which are known in the art. Linkages between nucleotides may be phosphodiester bonds or alternatives, for example, linking groups of the formula P(O)S, (thioate); P(S)S, (dithioate); P(O)NR'2; P(O)R'; P(O)OR6; CO; or CONR'2 wherein R is H (or a salt) or alkyl (1-12C) and R6 is alkyl (1-9C) is joined to adjacent nucleotides through —O— or —S—.

Alternatively, siRNA molecules or longer dsRNA molecules may be made recombinantly by transcription of a nucleic acid sequence, preferably contained within a vector as described below.

Modified nucleotide bases can be used in addition to the naturally occurring bases, and may confer advantageous properties on siRNA molecules containing them.

For example, modified bases may increase the stability of the siRNA molecule, thereby reducing the amount required for silencing. The provision of modified bases may also provide siRNA molecules which are more, or less, stable than unmodified siRNA.

The term 'modified nucleotide base' encompasses nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Thus modified nucleotides may also include 2'substituted sugars such as 2'-O-methyl-; 2-O-alkyl; 2-O-allyl; 2'-S-alkyl; 2'-S-allyl; 2'-fluoro-; 2'-halo or 2; azido-ribose, carbocyclic sugar analogues a-anomeric sugars; epimeric sugars such as arabinose, xyloses or lyxoses, pyranose sugars, furanose sugars, and sedoheptulose.

Modified nucleotides are known in the art and include alkylated purines and pyrimidines, acylated purines and pyrimidines, and other heterocycles. These classes of pyrimidines and purines are known in the art and include pseudoisocytosine, N4,N4-ethanocytosine, 8-hydroxy-N6-methyladenine, 4-acetylcytosine, 5-(carboxyhydroxylmethyl) uracil, 5 fluorouracil, 5-bromouracil, 5-carboxymethylaminomethyl-2-thiouracil, 5-carboxymethylaminomethyl uracil, dihydrouracil, inosine, N6-isopentyl-adenine, 1-methyladenine, 1-methylpseudouracil, 1-methylguanine, 2,2-dimethylguanine, 2-methyladenine, 2-methylguanine, 3-methylcytosine, 5-methylcytosine, N6-methyladenine, 7-methylguanine, 5-methylaminomethyl uracil, 5-methoxy amino methyl-2-thiouracil, -D-mannosylqueosine, 5-methoxycarbonylmethyluracil, 5-methoxyuracil, 2 methylthio-N6-isopentenyladenine, uracil-5-oxyacetic acid methyl ester, psueouracil, 2-thiocytosine, 5-methyl-2 thiouracil, 2-thiouracil, 4-thiouracil, 5-methyluracil, N-uracil-5-oxyacetic acid methylester, uracil 5-oxyacetic acid, queosine, 2-thiocytosine, 5-propyluracil, 5-propylcytosine, 5-ethyluracil, 5-ethylcytosine, 5-butyluracil, 5-pentyluracil, 5-pentylcytosine, and 2,6,diaminopurine, methylpsuedouracil, 1-methylguanine, 1-methylcytosine.

Vectors

The invention also provides vectors comprising a nucleotide sequence encoding an siRNA or longer RNA or DNA sequence for production of dsRNA. The vector may be any RNA or DNA vector. The vector is preferably an expression vector, wherein the nucleotide sequence is operably linked to a promoter compatible with the cell. The vector will preferably have at least two promoters, one to direct expression of the sense strand and one to direct expression of the antisense strand of the dsRNA. Alternatively, two vectors may be used, one for the sense strand and one for the antisense strand. Alternatively the vector may encode RNAs which form stem-loop structures which are subsequently cleaved by the cell to produce dsRNA.

Where the vector is an expression vector, the sequence to be expressed will preferably be operably linked to a promoter functional in the target cells. Promoters suitable for use in various vertebrate systems are well known. For example, suitable promoters include viral promoters such as mammalian retrovirus or DNA virus promoters, e.g. MLV, CMV, RSV, SV40 IEP and adenovirus promoters and metallothionein promoter. The CMV IEP may be more preferable for human use. Strong mammalian promoters may also be suitable as well as RNA polymerase II and III promoters. Variants of such promoters retaining substantially similar transcriptional activities may also be used.

Other vehicles suitable for use in delivering nucleic acids such as siRNAs include viruses and virus-like particles (VLPs) such as HPV VLPs comprising the L1 and/or L2 HPV viral protein; or hepatitis B viral proteins. Other suitable VLPs may be derived from picornaviruses; togaviruses; rhabdoviruses; orthomyxoviruses; retroviruses; hepadnaviruses; papovaviruses; adenoviruses; herpesviruses; and pox viruses.

Delivery

Various agents may be used to improve the delivery of RNA, DNA or protein into the cell. Viral vectors as described above may be used to deliver nucleic acid into a cell. Where other vectors, or no vector, is used, delivery agents such as liposomes may usefully be employed. Delivery peptides such as Antennapedia of the HIV TAT peptide may be used, as may organic polymers such as a dendrimers or polylysine-transferrine-conjugates.

Liposomes can be prepared from a variety of cationic lipids, including DOTAP, DOTMA, DDAB, L-PE, and the like. Lipid carrier mixtures containing a cationic lipid, such as N-[1-(2,3-dioleyloxy) propyl]-N,N,N-triethylammonium chloride (DOTMA) also known as "lipofectin", dimethyl dioctadecyl ammonium bromide (DDAB), 1,2-dioleoyloxy-3-(trimethylammonio) propane (DOTAP) or L-lysinyl-phosphatidylethanolamine (L-PE) and a second lipid, such as dioleoylphosphatidylethanolamine (DOPE) or cholesterol (Chol), are particularly useful for use with nucleic acids. DOTMA synthesis is described in Felgner, et al., (1987) Proc. Nat. Acad. Sciences, (USA) 84:7413-7417. DOTAP synthesis is described in Stamatatos, et al., Biochemistry, (1988) 27:3917-3925.

Liposomes are commercially available from many sources. DOTMA:DOPE lipid carriers can be purchased from, for example, BRL. DOTAP:DOPE lipid carriers can be purchased from Boehringer Mannheim. Cholesterol and DDAB are commercially available from Sigma Corporation. DOPE is commercially available from Avanti Polar Lipids. DDAB:DOPE can be purchased from Promega. Invitrogen make liposomes under the names Oligofectamine™ and Lipofectamine™.

To incorporate nucleic acid into liposomes, the liposome-nucleic acid complex is prepared by mixing with the nucleic acid in an appropriate nucleic acid:lipid ratio (for example 5:3) in a physiologically acceptable diluent (for example Opti-MEM™ at an appropriate dilution) immediately prior to use.

Apoptosis Assays

The induction of apoptosis in cells may be assayed by many methods. Apoptotic cells in culture may be detected and assayed by photomicrography; apoptotic cells may be detected by their distinctive morphology, with blebbing of the plasma membrane and chromatin condensation and fragmentation. DNA dyes such as propidium iodide (PI) or Hoechst 33342 may be used to detect chromatin condensation. Alternatively, TUNEL may be used to detect DNA strand breaks.

Antibodies such as anti-annexin V can be used to label apoptotic cells and detected by immunofluorescence, and assayed by micrography of FACS analysis.

FACS analysis may be used in combination with a DNA dye such as PI, TUNEL and/or annexin staining. Apoptotic cells may be detected as a sub-G1 fraction of cells which have lost DNA.

Release of cytochrome c from mitochondria is another marker for apoptosis. A measure of the early stages of apoptosis may be obtained by fractionating cell lysates into mitochondrial and cytoplasmic fractions and detecting the amount of cytochrome c released from the mitochondria into the cytosol. This is usually done by performing a Western blot and probing with an anti-cytochrome c antibody.

Proliferative Disease

A proliferative disease is a pathological condition characterised by unwanted cell growth. In general, proliferative diseases can be divided into two types: clonal and non-clonal. Clonal proliferative disease usually leads to the formation of tumours, which may be benign or malignant (cancerous). Cancers may be cancer of the skin, connective tissue, adipose, breast, lung, stomach, pancreas, ovary, cervix, uterus, kidney, bladder, colon, prostate, central nervous system (CNS), retina and circulating tumours (such as leukaemia and lymphoma). Colorectal cancer includes cancers of the colon, rectum, anus, and appendix.

SIRT inhibitors may be effective in providing treatments that discriminate between malignant and normal cells, avoiding many of the deleterious side-effects present with most current chemotherapeutic regimes.

Non-clonal proliferative diseases include psoriasis, fibrocystic disease, myelofibrosis, proliferative diabetic retinopathy, atherosclerosis (associated with proliferation of vascular cells) and chronic inflammatory proliferative diseases (CIPD).

As used herein, 'tumour cells' shall be taken to refer both to cells derived from tumours, including malignant tumours, and cells immortalised in vitro. 'Normal' cells refers to cells with normal growth characteristics that do not show abnormal proliferation.

'Therapy' and 'treatment' of disease includes any therapy or treatment that alleviates in any way the symptoms of a disease. These terms refer to any administration of the compound, salt or N-oxide thereof, intended to alleviate the severity of a disorder of the GI tract in a subject, and includes treatment intended to cure the disease, provide relief from the symptoms of the disease and to prevent or arrest the development of the disease in an individual at risk from developing the disease or an individual having symptoms indicating the development of the disease in that individual.

Compositions

Pharmaceutical compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

For solid compositions, conventional non-toxic solid carriers include, for example, pharmaceutical grades of mannitol, lactose, cellulose, cellulose derivatives, starch, magnesium stearate, sodium saccharin, talcum, glucose, sucrose, magnesium carbonate, and the like may be used. The active compound as defined above may be formulated as suppositories using, for example, polyalkylene glycols, acetylated triglycerides and the like, as the carrier. Liquid pharmaceutically administrable compositions can, for example, be prepared by dissolving, dispersing, etc, an active compound as defined above and optional pharmaceutical adjuvants in a carrier, such as, for example, water, saline aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see Remington's Pharmaceutical Sciences, 20th Edition, 2000, pub. Lippincott, Williams & Wilkins. The composition or formulation to be administered will, in any event, contain a quantity of the active compound(s) in an amount effective to alleviate the symptoms of the subject being treated.

Administration

Where a composition as described herein is to be administered to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. It will also depend upon toxicity of the therapeutic agent, as determined by pre-clinical and clinical trials.

Dosing is dependent on severity and responsiveness of the condition to be treated, with course of treatment lasting from several days to several months or until a diminution of disease state is achieved. Optimal dosing schedules are easily calculated from measurements of drug accumulation in the body. Persons of ordinary skill can easily determine optimum dosages, dosing methodologies and repetition rates. Therapeutically or prophylactically effective amounts (dosages) may vary depending on the relative potency of individual compositions, and can generally be routinely calculated based on molecular weight and EC50s in in vitro and/or animal studies. For example, given the molecular weight of an siRNA drug compound (derived from oligonucleotide sequence and chemical structure) and an experimentally derived effective dose such as an $IC_{50}$, for example, a dose in mg/kg is routinely calculated. In general, dosage is from 0.001 µg to 100 g and may be administered once or several times daily, weekly, monthly or yearly.

Compositions of the present invention may be administered in a number of ways depending upon whether local or systemic treatment is desired and upon the area to be treated. Administration may be topical (including ophthalmic, vaginal, rectal, intranasal, epidermal and transdermal), oral or parenteral. Parenteral administration includes intravenous drip, subcutaneous, intraperitoneal or intramuscular injection, pulmonary administration, e.g., by inhalation or insufflation, or intracranial, e.g., intrathecal or intraventricular, administration.

Prescription of treatment, e.g. decisions on dosage etc, is within the responsibility of general practitioners and other medical doctors. A composition may be administered alone or in combination with other treatments, either simultaneously or sequentially dependent upon the condition to be treated.

The invention is illustrated by the following examples.

Experimental Procedures

Design of siRNA Specific to SIRT1

A siRNA sequence located adjacent to the conserved sirtuin domain on the carboxy-terminal side was selected on the basis of its selectivity for SIRT1 and its predicted lack of secondary structure.

Bestfit matching to other sirtuin cDNAs was performed and the results were: SIRT2/3/7-57.9%; SIRT4/5/6-63.2%

BLAST searching of GenBank, EMBL, DDBJ and PDB databases was performed and the results were:

Matches 1-8: Human SIRT1 [some truncated clones].

Match 9: *Streptococcus* mutans sequence [imperfect].

Match 10: *Mus musculus* sequence [imperfect].

BLAST searching of the Genbank Human EST database was performed and the results were:

Matches 1-4: Human SIRT1.

Matches 5-10: Misc. sequences [imperfect].

These results showed that the selected sequence was likely to be specific for SIRT RNA.

The biophysical properties and predicted secondary structure formation of the selected sequence was:

| Tm: 46° C. | GC: 42.1% |
|---|---|
| Loop: No | Secondary structure: No |

Taken together, these results indicated that the selected sequence was likely to be effective in inducing RNA interference specific for the SIRT1 mRNA.

Control siRNAs were Lamin A/C siRNA (purchased from Dharmacon) and Bcr-AbI siRNA (siACE RNA, obtained from Dr Ming Jiang). A further control was the transfection of siRNA buffer alone (no siRNA).

RT-PCR

RT-PCR for SIRT1, Lamin A/C, BCR-AbI and controls (vimentin and GAPDH) was performed. A SIRT1 upstream [5'] primer located in conserved core domain, over an exon-exon boundary, and a downstream [3'] primer located in SIRT1-specific sequence were selected.

RT-PCR was performed from total RNA using a Reverse-It One-Step kit (ABgene) according to the manufacturer's instructions, and visualised on 2% TAE gels with ethidium bromide. Primers are shown in the sequence tables as Table 1.

Western Blotting

Cells for protein lysates were washed in PBS and lysed in buffer IPAX (10 mM TRIS base pH 8.0, 140 mM NaCl, 0.5% NP40, 1 mM PMSF, 1× Complete Protease Inhibitors (Roche), 50 mM NaF, 1 mM $Na_3VO_4$, 1 µM trichostatin A, 10 mM nicotinamide). Lysates were spun at 13 000 g for 20 minutes at 4° C. to separate soluble and insoluble fractions, where indicated. Mitochondrial and cytosolic fractions were prepared as previously described (Marsden et al., 2002), where indicated. Lysates were run on 10% or 15% SDS-PAGE, electroblotted to Protran membrane (Schleicher & Schuell), and probed with antibodies as described below. Visualisation was with the POD chemiluminescence kit (Roche).

Blots were probed with the following antibodies: anti-SIRT1 (H-300, Santa Cruz); anti-p53 (DO-1, Oncogene); anti-phosphoserine 15 (Ser15-R, Santa Cruz), anti-p21 (SX118, Pharmingen); anti-HDM2 (monoclonal antibody 4B2, prepared in-house); anti-lamin A/C (636, Santa Cruz); Anti-AbI (8E9, Pharmingen); anti-Bax (N-20, Santa Cruz); anti-PUMAα (AHP727, Serotec) and anti-cytochrome c (7H, 8.2; C12, Pharmingen).

Photomicrography

Phase contrast images were captured with an Axiovert 200M Cell Observer platform (Zeiss) at various time points post-transfection.

Cell Cycle Analysis

Cells were fixed with 70% ethanol at −20° C., washed with PBS and incubated for 15 minutes at room temperature in PBS containing 10U $ml^{-1}$ RNaseA and 30 $µml^{1}$ propidium iodide. Samples were analysed on a FACSCalibur flow cytometer (Beckton Dickinson) using CellQuest software.

Results

Example 1

Inhibition of SIRT Expression by RNAi

A siRNA specific to human SIRT1 was designed which had no more than ~60% homology to any other human sirtuin cDNA (Table 2). BLAST searching of human genomic and EST databases reported only the SIRT1 gene itself as a significant match. As a positive control we used an siRNA directed to lamin A/C (Dharmacon; Elbashir et al., 2001) (Table 2); as a negative control we used an siRNA directed to the BCR-ABL fusion oncogene (MWG-Biotech) which is biologically active only in a background of BCR-ABL (Table 2). The siRNAs were introduced to wild-type or $p53^{-/-}$ or $Bax^{-/-}$ HCT116 colorectal cancer cells by cationic-based lipid transfection (Oligofectamine™, Invitrogen) according to the manufacturer's instructions. Cells were harvested 48 hours post-transfection for the preparation of total cellular RNA and at 12 hour intervals post-transfection for the preparation of protein lysates and protein lysates.

One-step RT-PCR showed that only the SIRT1 siRNA reduced the abundance of SIRT1 mRNA; the mock transfections and control siRNAs did not alter SIRT1 mRNA. RT-PCR specific for the lamin A mRNA demonstrated that the lamin A/C siRNA was active in HCT116 cells, and therefore that an active siRNA process does not alter SIRT1 mRNA.

Additionally, silencing of SIRT1 mRNA did not alter lamin A mRNA, and none of the siRNAs altered abundance of the mRNAs chosen as controls, vimentin and GAPDH. These data support the specificity of the SIRT1 siRNA for RNAi.

Western blots were performed to establish the efficacy of RNAi in inhibiting protein expression. First, a western blot of whole cell lysates from cells transfected with SIRT1 siRNA, Lamin A/C siRNA and Bcr-AbI siRNA was prepared, and probed with an anti-SIRT1 antibody and an anti-Lamin A/C antibody. Next, a western blot of the soluble fraction of lysates from $p53^{+/+}$ cells and $p53^{-/-}$ cells transfected with SIRT1 siRNA, Lamin A/C siRNA and Bcr-AbI siRNA was performed. Equal amounts of total protein were loaded in each lane. Blots were probed with an anti-SIRT1 antibody and 2 minute and 10 minute exposure times used. Thirdly, western blot of the soluble fraction of lysates from $p53^{+/+}$ cells and $p53^{-/-}$ cells transfected with SIRT1 siRNA, Lamin A/C siRNA and Bcr-AbI siRNA were probed with an anti-SIRT1 antibody.

It was found that only LaminA/C siRNAs silence Lamin A protein expression in $p53^{+/+}$ cells and $p53^{-/-}$ cells under optimal growth conditions, but silencing of SIRT1 can downregulate Lamin A if cellular stress is applied. (Note that the antibody used did not seem to recognise Lamin A in whole cell lysates). The data confirms that BCR-AbI siRNA does not induce RNAi in cells lacking BCR-ABL. Overall, the results demonstrate the efficacy of SIRT1 siRNA in reducing SIRT1 protein expression.

Significant silencing at the protein level was observed for LaminA/C which had not been indicated by the RT-PCR. This suggests that the relationship between silencing at the mRNA and protein levels is not linear. Likewise, the blots probed for SIRT1 showed a profound silencing at the protein level although RT-PCR had shown only ~50% mRNA degradation. Possibly this reflects protection or sequestration of a pool of the mRNA, such that it is not accessible to components of the RNAi machinery.

Example 2

Effect of SIRT1 siRNA on p53 Stability and Activity

We went on the investigate the effect of SIRT1 siRNA on p53 stability and activity. In response to cellular stress, it appears that stabilisation of p53 requires only its prior destabilisation by HDM2 (Blattner et al., 1999). The most significant post-translational modification in this regard is phosphorylation of serine 20, now generally accepted as the major mechanism through which p53 is removed from HDM2-mediated negative regulation (Chehab et al., 1999; Dumaz et al., 2001). Phosphorylation of serine 15, previously thought to be involved in stabilisation of p53 (Shieh et al., 1997; Unger et al., 1999), is now believed to be primarily involved in the activation of p53 as a transcription factor (Dumaz and Meek, 1999). The acetylation of the carboxy-terminus of p53 occurs in response to most stimuli that stabilise p53 (Itoh et al., 2001).

Although the function of acetylation of p53 is not fully understood it appears to be stimulated by phosphorylation of serine 15 (Dumaz and Meek, 1999; Lambert et al., 1998), implicated in nucleotide excision repair (Rubbi and Milner, 2003) and in the recruitment of acetylase enzymes to chromatin (Espinosa and Emerson, 2001), and required for efficient p53-dependent apoptosis (Luo et al., 2001; Vaziri et al., 2001). Although it has been demonstrated that, under certain circumstances, neither amino-terminal phosphorylation nor carboxy-terminal acetylation are obligate events for the stabilisation and activation of p53 (Blattner et al., 1999; Ashcroft et al., 2000), the weight of evidence supports a general model whereby stress stimuli signal to p53 via phosphorylation of amino-terminal serine residues. These phosphorylations stabilise p53 and promote interaction with acetylase enzymes; acetylation of the carboxy-terminus fully activates p53 as a transcription factor and may help stabilise p53 (Nakamura et al., 2000).

To determine if silencing of SIRT1 could stabilise p53, we performed Western blots using the pantropic anti-p53 antibody DO-1 in cells treated with SIRT1.

Whole cell lysates, soluble and insoluble fractions from cells were transfected with SIRT1 siRNA, Lamin A/C siRNA and Bcr-AbI siRNA, blotted and probed with an anti-p53 antibody. Secondly, a western blot of whole cell lysates, soluble and insoluble fractions of lysates from $p53^{+/+}$ cells and $p53^{-/-}$ cells transfected with SIRT1 siRNA, Lamin A/C siRNA and Bcr-AbI siRNA and probed with an anti-p53 antibody was prepared. Recombinant human p53 was run as an antibody control.

The results revealed that silencing of SIRT1 led to a significant stabilisation of p53 compared to the mock transfected control. It is possible that the RNAi process itself constitutes a low-level stress signal, as a small stabilisation of p53 was observed for the lamin A/C siRNA but not the BCR-ABL siRNA. Interestingly, the p53 stabilised by the SIRT1 siRNA was partitioned between the soluble (cytoplasmic and nucleoplasmic) fraction and the insoluble fraction protein, thought the p53 stabilised by LaminA/C silencing was found only in the soluble fraction.

We then examined in more detail the stabilisation and activation of p53 in HCT116 cells transfected with SIRT1 siRNA. Western blots of whole cell lysates, soluble and insoluble fractions from cells transfected with SIRT1 siRNA and probed with either the anti-p53 antibody DO-1 or an anti-phosphoSer15 antibody were prepared. A further blot was probed with antibodies to p21 and HDM2. Cells were harvested at 12, 24, 36 and 48 hours post-transfection. Further, a western blot of whole cell lysates, soluble and insoluble fractions of lysates from $p53^{+/+}$ cells transfected with SIRT1 siRNA, Lamin A/C siRNA and Bcr-AbI siRNA were prepared, and probed with an anti-phosphoSer15 antibody. Recombinant human p53 was run as an antibody control.

A further western blot of whole cell lysates from cells transfected with SIRT1 siRNA, Lamin A/C siRNA and Bcr-AbI siRNA and probed with an anti-phosphoSer15 antibody was also prepared.

Significant stabilisation of p53 was not observed in whole cell lysates until 36 hours post-transfection, although the soluble fraction showed that there was stabilisation at 24 hours. Intriguingly, stabilised p53 was not detected in the insoluble fraction until 36 hours post-transfection, and was not highly elevated until 48 hours.

To analyse the activation of p53 as a transcription factor we examined phosphorylation of serine 15 by western blotting as described above. We determined that stabilised p53 was not subject to serine 15 phosphorylation prior to 36 hours post-transfection. Furthermore, that serine 15 phosphorylation was restricted to p53 in the soluble fraction, as no phosphorylation of this residue was detected at any time point in the insoluble fraction. LaminA/C silencing can induce a very small amount of phosphorylation, and BCR-ABL siRNAs do not stimulate phosphorylation.

This data is somewhat counter-intuitive, as one might assume that transcriptionally competent p53 would be associated with chromatin. However, these cells were cultured under normal conditions and in the absence of any exogenous stress stimulus. It was therefore possible that although the p53 was stabilised and "activated", additional signals or cofactors not present or accessible to the p53 under these conditions were required to activate gene transcription.

Example 3

Effect of SIRT1 siRNA on Downstream Activity of p53

To investigate this, we analysed expression of the two best-characterised p53 responsive genes, p21(CIP1/WAF1) and HDM2.

In addition to the blot probed with antibodies to p21 and HDM2 described above, a further western blot of soluble lysates from p53$^{+/+}$ cells and p53$^{-/-}$ cells transfected with SIRT1 siRNA, Lamin A/C siRNA and Bcr-AbI siRNA and probed with an anti-p21 antibody was prepared. A second blot of whole cell lysates from p53$^{+/+}$ cells incubated at 37° C. and subjected to cold shock and transfected with SIRT1 siRNA, Lamin A/C siRNA and Bcr-AbI siRNA and probed with an anti-p21 antibody was also prepared. It was observed that SIRT1 inhibition does not induce p21 expression under conditions of cold shock.

The results for these were essentially identical, as both showed a strong induction of expression at 36 hours that was absent prior to this time point. There was therefore a good temporal correlation in this data between stabilisation of p53, "activating" post-translational modification, and the induction of transcriptional targets. This effect was seen only in p53$^{+/+}$ cells, indicating that the p21 expression was indeed induced by p53. Silencing of SIRT1 does not induce expression of p21 if cellular stress is applied.

Example 4

SIRT1 siRNA Induces Apoptosis in Tumour Cells Independently of p53

As p21 was effectively induced, we wondered if these cells were cell cycle arrested. Phase contrast images were taken of HCT116 p53$^{+/+}$ cells 24 hours and 48 hours after transfection with SIRT1 siRNA, BCR-AbI siRNA and Lamin A/C siRNA, and also of HCT116 p53$^{+/+}$ cells at 12 hour timepoints after transfection with SIRT siRNA. Additional phase contrast images of HCT116 p53$^{-/-}$ cells 24 hours, 48 hours after transfection with SIRT1 siRNA, BCR-AbI siRNA and Lamin A/C siRNA were taken.

The images showed a very clear phenotype that was apparent at 36 hours, and pronounced by 48 hours. Close examination of these cells under higher magnification revealed reduction of the cell bodies, extensive membrane blebbing and a granular appearance to the nucleus.

Surprisingly, this effect was also seen in p53$^{-/-}$ cells as well as p53$^{+/+}$ cells, indicating that the apoptosis observed was not occurring via a p53-dependent pathway, counter to previous findings.

As these morphological changes are typical of apoptosis, we analysed control and SIRT1-silenced HCT116 p53$^{+/+}$ cells by flow cytometry. Cells were analysed at 48 hours post-transfection. Propidium iodide staining revealed that there was no significant change in the cell cycle profile of cells transfected with either the lamin A/C or BCR-ABL siRNAs, as compared to the mock-transfected controls. Cells treated with the SIRT1 siRNA showed a marked decrease of the G1 and G2/M populations and a significant increase in sub-G1 population, consistent with apoptotic chromatin fragmentation.

As cells treated with SIRT1 siRNA were clearly undergoing apoptosis, we next considered whether in p53$^{+/+}$ cells the stabilised p53 induced the expression of components of the pro-apoptotic machinery. Activation of p53 in HCT116 cells has previously been demonstrated to induce expression of two pro-apoptotic genes, PUMA and Bax (Yu et al., 2003; Zhang et al., 2000). Thus, western blots of lysates from cells transfected with SIRT1 siRNA were probed with an anti-Bax antibody and an anti-PUMA antibody were performed to determine Bax and PUMA expression in cells treated with SIRT1 siRNA.

Neither Bax nor PUMA was induced in SIRT1-silenced cells, as compared to the controls. Indeed, PUMA appeared to be repressed by transfection of the cells with SIRT1 siRNA. Further, SIRT siRNA induced apoptosis even in p53$^{+/+}$ cells lacking Bax, as determined from phase contrast images of HCT116 p53$^{+/+}$Bax$^{-/-}$ cells 24 hours and 48 hours and after transfection with SIRT1 siRNA. These results indicate that SIR1 siRNA can induce apoptosis via a p53-independent mechanism even in p53$^{+/+}$ cells.

Two modes of apoptosis are present in human cells: The intrinsic pathway, which functions through mitochondria, and the extrinsic pathway, which functions through the activation of cell death receptors (for review see Green, 1998). PUMA and Bax are both components of the intrinsic pathway, and as neither was induced by the stabilised p53, it was necessary to determine which apoptotic pathway had been activated.

The discovery of cross-talk between the intrinsic and extrinsic pathways (Green, 1998) has been complicated by the discovery that cell type determines the extent of cross-talk. This has led to the idea that cells fall into one of two types. Type I cells can undergo death receptor induced apoptosis independently of mitochondria; type II cells require mitochondrial involvement for death receptor signalling to induce apoptosis (Scaffidi et al., 1998). Importantly, it has been established that HCT116 cells exhibit the behaviour of type II cells (Deng et al., 2002), which implies that the apoptosis induced by SIRT1 treatment most likely functions through mitochondria.

Example 5

SIRT1 siRNA does not Induce Apoptosis in Normal Cells

We decided to test the effect of SIRT1 siRNA on a non-tumour cell line. Phase contrast images of primary human normal diploid fibroblasts (NDFs) transfected with SIRT1 siRNA, were taken at 2, 3, 4 and 5 days post-transfection. This treatment not only failed to provoke the massive apoptosis seen in HCT116 cells, it did not appear to induce apoptosis at all. Cells were still healthy 5 days post-transfection.

We have demonstrated that silencing of SIRT1 in HCT116 colorectal cancer cells provokes massive apoptosis. The tumour suppressor p53 is stabilised in response to SIRT1 silencing, and undergoes at least partial activation for transcriptional function. This effect is independent of p53, and we did not detect induction of either PUMA or Bax, two pro-apoptotic genes that have been shown to be critical for p53-dependent apoptosis in colorectal cancer cells. Moreover, apoptosis was not induced by SIRT1 siRNA in normal cells, indicating this effect may be specific to tumour cells.

REFERENCES

Appella E and Anderson C W. (2001). Eur. J. Biochem., 268, 2764-2772.
Ashcroft M, Taya Y and Vousden K H. (2000). Mol. Cell. Biol., 20, 3224-3233.
Blattner C, Tobiasch E, Liffen M, Rahmsdorf H J and Herrlich P. (1999). Oncogene, 18, 1723-1732.
Chehab N H, Malikzay A, Stavridi E S and Halazonetis T D. (1999). Proc. Natl. Acad. Sci. USA, 96, 13777-13782.
Dumaz N and Meek D W. (1999). Embo J., 18, 7002-7010.
Dumaz N, Milne D M, Jardine L J and Meek D W. (2001). Biochem. J., 359, 459-464.
Elbashir S M, Harborth J, Lendeckel W, Yalcin A, Weber K and Tuschl T. (2001). Nature, 411, 494-498.
Espinosa J M and Emerson B M. (2001). Mol. Cell, 8, 57-69.
Frye R. (1999). Biochem. Biophys. Res. Commun., 273, 793-798.
Green D R. (1998). Cell, 94, 695-698.
Ito A, Lai C—H, Zhao X, Saito S, Hamilton M H, Appella E and Yao, T-P. (2001). EMBO J., 20, 1331-1340.
Jiang M and Minler J. (2002). Oncogene, 21, 6041-6048.
Jiang M and Milner J. (2003). Genes Dev., 17, 832-837.
Juan L-J, Shia W J, Chen M H, Yang, W M, Seto E, Lin Y S and Wu C W. (2000). J. Biol. Chem., 275, 20436-20443.
Lambert P F, Kashanchi F, Radonovich M F, Shiekhattar R and Brady J N. (1998). J. Biol. Chem., 273, 33048-33053.
Langley, E. et al., (2002) EMBO J 21/2383-2396.
Luo J, Nikolaev A Y, Imai S, Chen D, Su F, Shiloh A, Guarente L and Gu W. (2001). Cell, 107, 137-148.
Luo J, Su F, Chen D, Shiloh A and Gu W. (2000). Nature, 408, 377-381.
Marsden V S, O'Connor L, O'Reilly L A, Silke J, Metcalf D, Ekert P G, Huang D C, Cecconi F, Kuida K, Tomaselli K J, Roy S, Nicholson D W, Vaux D L, Bouillet P, Adams J M and Strasser A. (2002). Nature, 419, 634-637.
Murphy M, Ahn J, Walker K K, Hoffman W H, Evans R M, Levine A J and George D L. (1999). Genes Dev., 13, 2490-2501.
Nakamura S, Roth J A and Mukhopadhyay T. (2000). Mol. Cell. Biol., 20, 3224-3233.
Pluquet 0 and Hainaut P. (2001). Cancer Lett., 174, 1-15.
Rosenberg M I and Parkhurst S M. (2002). Cell, 109, 447-458.
Rubbi C P and Milner J. (2003). EMBO J., 22, 975-986.
Scaffidi C, Fulda S, Srinvasan A, Friesen C, Li F, Tomaselli K J, Debatin K-M, Kramer P H and Peter M E. (1998). EMBO J., 17, 1675-1687.
Shieh S-Y, Ikeda M, Taya C and Prives C. (1997). Cell, 91, 325-334.
Takata T and Ishikawa F. (2002). Biochem. Biophys. Res. Commun., 301, 250-257.
Unger T, Juven-Gershon T, Moallem E, Berger M, Vogt Sionov R, Lozano G, Oren M and Haupt Y. (1999). EMBO J., 18, 1805-1814.
Vaziri H, Dessain S K, Ng Eaton E, Imai S, Frye R, Pandita T K, Guarente L and Weinberg R A. (2001). Cell, 107, 149-159.
Yu J, Zhenghe W, Kinzler K W, Vogelstein B and Zhang L. (2003). Proc. Natl. Acad. Sci. USA, 100, 1931-1936.
Zhang L, Yu J, Ho Park B, Kinzler K W and Vogelstein B. (2000). Science, 290, 989-992.

Sequence Tables:

TABLE 1

| PCR Primers | | |
|---|---|---|
| SIRT1 sense | 5'-TCAGTGTCATGGTTCCTTTGC-3' | (SEQ ID NO: 3) |
| SIRT1 antisense | 5'-AATCTGCTCCTTTGCCACTCT-3' | (SEQ ID NO: 4) |
| Lamin A sense | 5'-AAGCAGCGTGAGTTTGAGAGC-3' | (SEQ ID NO: 5) |
| Lamin A antisense | 5'-AGGGTGAACTTTGGTGGGAAC-3' | (SEQ ID NO: 6) |
| GAPDH sense | 5'-CGGAGTCAACGGATTTGGTCGTAT-3' | (SEQ ID NO: 7) |
| GAPDH antisense | 5'-AGCCTTCTCCATGGTGGTGAAGAC-3' | (SEQ ID NO: 8) |
| Vimentin sense | 5'-gCCAACTACATCgACAAggTg-3' | (SEQ ID NO: 9) |
| Vimentin antisense | 5'-gAgCAggTCTTggTATTCACg-3' | (SEQ ID NO: 10) |

TABLE 2

| | siRNA Sequences | | |
|---|---|---|---|
| SIRT1 | 5' acuuugcuguaaccuguatt 3' | (SEQ ID NO: 11) |
| | 3' ttugaaacgacauugggacau 5' | (SEQ ID NO: 12) |
| Lamin A/C | 5' cuggacuuccagaagaacatt 3' | (SEQ ID NO: 13) |
| | 3' ttgaccugaaggucuucuugu 5' | (SEQ ID NO: 14) |
| BCR-ABL | 5' agaguucaaaagcccuucatt 3' | (SEQ ID NO: 15) |
| | 3' ttucucaaguuuucgggaagu 5' | (SEQ ID NO: 16) |

TABLE 3 cDNA sequence of human SIRT1 (SEQ ID NO: 1). The locations, and sequences, of PCR primers and the siRNAs described herein are also indicated.

```
   1 ATGGCGGACG AGGCGGCCCT CGCCCTTCAG CCCGGCGGCT CCCCCTCGGC
     TACCGCCTGC TCCGCCGGGA GCGGGAAGTC GGGCCGCCGA GGGGGAGCCG

51 GGCGGGGGCC GACAGGGAGG CCGCGTCGTC CCCCGCCGGG GAGCCGCTCC
     CCGCCCCCGG CTGTCCCTCC GGCGCAGCAG GGGGCGGCCC CTCGGCGAGG

101 GCAAGAGGCC GCGGAGAGAT GGTCCCGGCC TCGAGCGGAG CCCGGGCGAG
     CGTTCTCCGG CGCCTCTCTA CCAGGGCCGG AGCTCGCCTC GGGCCCGCTC

151 CCCGGTGGGG CGGCCCCAGA GCGTGAGGTG CCGGCGGCGG CCAGGGGCTG
     GGGCCACCCC GCCGGGGTCT CGCACTCCAC GGCCGCCGCC GGTCCCCGAC

201 CCCGGGTGCG GCGGCGGCGG CGCTGTGGCG GGAGGCGGAG GCAGAGGCGG
     GGGCCCACGC CGCCGCCGCC GCGACACCGC CCTCCGCCTC CGTCTCCGCC

251 CGGCGGCAGG CGGGGAGCAA GAGGCCCAGG CGACTGCGGC GGCTGGGGAA
     GCCGCCGTCC GCCCCTCGTT CTCCGGGTCC GCTGACGCCG CCGACCCCTT

301 GGAGACAATG GGCCGGGCCT GCAGGGCCCA TCTCGGAGC CACCGCTGGC
     CCTCTGTTAC CCGGCCCGGA CGTCCCGGGT AGAGCCCTCG GTGGCGACCG

351 CGACAACTTG TACGACGAAG ACGACGACGA CGAGGGCGAG GAGGAGGAAG
     GCTGTTGAAC ATGCTGCTTC TGCTGCTGCT GCTCCCGCTC CTCCTCCTTC

401 AGGCGGCGGC GGCGGCGATT GGGTACCGAG ATAACCTTCT GTTCGGTGAT
     TCCGCCGCCG CCGCCGCTAA CCCATGGCTC TATTGGAAGA CAAGCCACTA

451 GAAATTATCA CTAATGGTTT TCATTCCTGT GAAAGTGATG AGGAGGATAG
     CTTTAATAGT GATTACCAAA AGTAAGGACA CTTTCACTAC TCCTCCTATC

501 AGCCTCACAT GCAAGCTCTA GTGACTGGAC TCCAAGGCCA CGGATAGGTC
     TCGGAGTGTA CGTTCGAGAT CACTGACCTG AGGTTCCGGT GCCTATCCAG

551 CATATACTTT TGTTCAGCAA CATCTTATGA TTGGCACAGA TCCTCGAACA
     GTATATGAAA ACAAGTCGTT GTAGAATACT AACCGTGTCT AGGAGCTTGT

601 ATTCTTAAAG ATTTATTGCC GGAAACAATA CCTCCACCTG AGTTGGATGA
     TAAGAATTTC TAAATAACGG CCTTTGTTAT GGAGGTGGAC TCAACCTACT

651 TATGACACTG TGGCAGATTG TTATTAATAT CCTTTCAGAA CCACCAAAAA
     ATACTGTGAC ACCGTCTAAC AATAATTATA GGAAAGTCTT GGTGGTTTTT

701 GGAAAAAAAG AAAAGATATT AATACAATTG AAGATGCTGT GAAATTACTG
     CCTTTTTTTC TTTTCTATAA TTATGTTAAC TTCTACGACA CTTTAATGAC

751 CAAGAGTGCA AAAAAATTAT AGTTCTAACT GGAGCTGGGG TGTCTGTTTC
     GTTCTCACGT TTTTTTAATA TCAAGATTGA CCTCGACCCC ACAGACAAAG

801 ATGTGGAATA CCTGACTTCA GGTCAAGGGA TGGTATTTAT GCTCGCCTTG
     TACACCTTAT GGACTGAAGT CCAGTTCCCT ACCATAAATA CGAGCGGAAC

851 CTGTAGACTT CCCAGATCTT CCAGATCCTC AAGCGATGTT TGATATTGAA
     GACATCTGAA GGGTCTAGAA GGTCTAGGAG TTCGCTACAA ACTATAACTT

901 TATTTCAGAA AAGATCCAAG ACCATTCTTC AAGTTTGCAA AGGAAATATA
     ATAAAGTCTT TTCTAGGTTC TGGTAAGAAG TTCAAACGTT TCCTTTATAT

951 TCCTGGACAA TTCCAGCCAT CTCTCTGTCA CAAATTCATA GCCTTGTCAG
     AGGACCTGTT AAGGTCGGTA GAGAGACAGT GTTTAAGTAT CGGAACAGTC

1001 ATAAGGAAGG AAAACTACTT CGCAACTATA CCCAGAACAT AGACACGCTG
     TATTCCTTCC TTTTGATGAA GCGTTGATAT GGGTCTTGTA TCTGTGCGAC

2T1PH0
                                       T CAGTGTCATG GTTCCTTTGC
1051 GAACAGGTTG CGGGAATCCA AAGGATAATT CAGTGTCATG*GTTCCTTTGC
     CTTGTCCAAC GCCCTTAGGT TTCCTATTAA GTCACAGTAC*CAAGGAAACG

1101 AACAGCATCT TGCCTGATTT GTAAATACAA AGTTGACTGT GAAGCTGTAC
     TTGTCGTAGA ACGGACTAAA CATTTATGTT TCAACTGACA CTTCGACATG

1151 GAGGAGATAT TTTTAATCAG GTAGTTCCTC GATGTCCTAG GTGCCCAGCT
     CTCCTCTATA AAAATTAGTC CATCAAGGAG CTACAGGATC CACGGGTCGA
```

TABLE 3-continued cDNA sequence of human SIRT1 (SEQ ID NO: 1). The locations, and sequences, of PCR primers and the siRNAs described herein are also indicated.

```
1201 GATGAACCGC TTGCTATCAT GAAACCAGAG ATTGTGTTTT TTGGTGAAAA
     CTACTTGGCG AACGATAGTA CTTTGGTCTC TAACACAAAA AACCACTTTT

1251 TTTACCAGAA CAGTTTCATA GAGCCATGAA GTATGACAAA GATGAAGTTG
     AAATGGTCTT GTCAAAGTAT CTCGGTACTT CATACTGTTT CTACTTCAAC

1301 ACCTCCTCAT TGTTATTGGG TCTTCCCTCA AAGTAAGACC AGTAGCACTA
     TGGAGGAGTA ACAATAACCC AGAAGGGAGT TTCATTCTGG TCATCGTGAT

1351 ATTCCAAGTT CCATACCCCA TGAAGTGCCT CAGATATTAA TTAATAGAGA
     TAAGGTTCAA GGTATGGGGT ACTTCACGGA GTCTATAATT AATTATCTCT

1401 ACCTTTGCCT CATCTGCATT TTGATGTAGA GCTTCTTGGA GACTGTGATG
     TGGAAACGGA GTAGACGTAA AACTACATCT CGAAGAACCT CTGACACTAC

~~~~
                                                    ACUU
1451 TCATAATTAA TGAATTGTGT CATAGGTTAG GTGGTGAATA TGCCAAACTT
     AGTATTAATT ACTTAACACA GTATCCAATC CACCACTTAT ACGGTTTGAA
                                                    dTdTUGAA rJF3
     UGCUGUAACC CUGUAdTdT
1501 TGCTGTAACC CTGTAAAGCT TTCAGAAATT ACTGAAAAAC CTCCACGAAC
     ACGACATTGG GACATTTCGA AAGTCTTTAA TGACTTTTTG GAGGTGCTTG
     ACGACAUUGG GACAU
         rJF4

1551 ACAAAAAGAA TTGGCTTATT TGTCAGAGTT GCCACCCACA CCTCTTCATG
     TGTTTTTCTT AACCGAATAA ACAGTCTCAA CGGTGGGTGT GGAGAAGTAC

1601 TTTCAGAAGA CTCAAGTTCA CCAGAAAGAA CTTCACCACC AGATTCTTCA
     AAAGTCTTCT GAGTTCAAGT GGTCTTTCTT GAAGTGGTGG TCTAAGAAGT

1651 GTGATTGTCA CACTTTTAGA CCAAGCAGCT AAGAGTAATG ATGATTTAGA
     CACTAACAGT GTGAAAATCT GGTTCGTCGA TTCTCATTAC TACTAAATCT

1701 TGTGTCTGAA TCAAAAGGTT GTATGGAAGA AAAACCACAG GAAGTACAAA
     ACACAGACTT AGTTTTCCAA CATACCTTCT TTTTGGTGTC CTTCATGTTT

1751 CTTCTAGGAA TGTTGAAAGT ATTGCTGAAC AGATGGAAAA TCCGGATTTG
     GAAGATCCTT ACAACTTTCA TAACGACTTG TCTACCTTTT AGGCCTAAAC

1801 AAGAATGTTG GTTCTAGTAC TGGGGAGAAA AATGAAAGAA CTTCAGTGGC
     TTCTTACAAC CAAGATCATG ACCCCTCTTT TTACTTTCTT GAAGTCACCG

1851 TGGAACAGTG AGAAAATGCT GGCCTAATAG AGTGGCAAAG GAGCAGATTA
     ACCTTGTCAC TCTTTTACGA CCGGATTATC TCACCGTTTC CTCGTCTAAT
                                                 TC TCACCGTTTC CTCGTCTAA
                                                        2T1REV

1901 GTAGGCGGCT TGATGGTAAT CAGTATCTGT TTTTGCCACC AAATCGTTAC
     CATCCGCCGA ACTACCATTA GTCATAGACA AAAACGGTGG TTTAGCAATG

1951 ATTTTCCATG GCGCTGAGGT ATATTCAGAC TCTGAAGATG ACGTCTTATC
     TAAAAGGTAC CGCGACTCCA TATAAGTCTG AGACTTCTAC TGCAGAATAG

2001 CTCTAGTTCT TGTGGCAGTA ACAGTGATAG TGGGACATGC CAGAGTCCAA
     GAGATCAAGA ACACCGTCAT TGTCACTATC ACCCTGTACG GTCTCAGGTT

2051 GTTTAGAAGA ACCCATGGAG GATGAAAGTG AAATTGAAGA ATTCTACAAT
     CAAATCTTCT TGGGTACCTC CTACTTTCAC TTTAACTTCT TAAGATGTTA

2101 GGCTTAGAAG ATGAGCCTGA TGTTCCAGAG AGAGCTGGAG GAGCTGGATT
     CCGAATCTTC TACTCGGACT ACAAGGTCTC TCTCGACCTC CTCGACCTAA

2151 TGGGACTGAT GGAGATGATC AAGAGGCAAT TAATGAAGCT ATATCTGTGA
     ACCCTGACTA CCTCTACTAG TTCTCCGTTA ATTACTTCGA TATAGACACT

2201 AACAGGAAGT AACAGACATG AACTATCCAT CAAACAAATC A
     TTGTCCTTCA TTGTCTGTAC TTGATAGGTA GTTTGTTTAG T
```

TABLE 4

HSIRT1 Protein Sequence (SEQ ID NO: 2)

| | |
|---|---|
| MADEAALALQPGGSPSAAGADREAASSPAGEPLRKRPRRDGPGLERSPGEPGGAAPEREV | 60 |
| PAAARGCPGAAAAALWREAEAEAAAAGGEQEAQATAAAGEGDNGPGLQGPSREPPLADNL | 120 |
| YDEDDDDEGEEEEAAAAAIGYRDNLLFGDEIITNGFHSCESDEEDRASHASSSDWTPRP | 180 |
| RIGPYTFVQQHLMIGTDPRTILKDLLPETIPPPELDDMTLWQIVINILSEPPKRKKRKDI | 240 |
| NTIEDAVKLLQECKKIIVLTGAGVSVSCGIPDFRSRDGIYARLAVDFPDLPDPQAMFDIE | 300 |
| YFRKDPRPFFKFAKEIYPGQFQPSLCHKFIALSDKEGKLLRNYTQNIDTLEQVAGIQRII | 360 |
| QCHGSFATASCLICKYKVDCEAVRGDIFNQVVPRCPRCPADEPLAIMKPEIVFFGENLPE | 420 |
| QFHRAMKYDKDEVDLLIVIGSSLKVRPVALIPSSIPHEVPQILINREPLPHLHFDVELLG | 480 |
| DCDVIINELCHRLGGEYAKLCCNPVKLSEITEKPPRTQKELAYLSELPPTPLHVSEDSSS | 540 |
| PERTSPPDSSVIVTLLDQAAKSNDDLDVSESKGCMEEKPQEVQTSRNVESIAEQMENPDL | 600 |
| KNVGSSTGEKNERTSVAGTVRKCWPNRVAKEQISRRLDGNQYLFLPPNRYIFHGAEVYSD | 660 |
| SEDDVLSSSSCGSNSDSGTCQSPSLEEPMEDESEIEEFYNGLEDEPDVPERAGGAGFGTD | 720 |
| GDDQEAINEAISVKQEVTDMNYPSNKS | 747 |

---

The invention claimed is:

1. A siRNA which inhibits expression of SIRT1 in a cell which siRNA comprises the sequence:

5' acuuugcuguaacccuguatt 3'     (SEQ ID NO: 11)

3' ttugaaacgacauugggacau 5',    (SEQ ID NO: 12)

wherein the tt overhangs are present or absent, wherein said siRNA is up to 22 bp in length.

2. A siRNA according to claim 1 which is 19 bp in length.

3. A composition comprising a siRNA according to claim 1 and a pharmaceutically acceptable excipient.

* * * * *